United States Patent
Safar

(10) Patent No.: US 11,534,014 B2
(45) Date of Patent: Dec. 27, 2022

(54) PROTECTION SHEET DISPENSER

(71) Applicant: Samir Hanna Safar, San Diego, CA (US)

(72) Inventor: Samir Hanna Safar, San Diego, CA (US)

( * ) Notice: Subject to any disclaimer, the term of this patent is extended or adjusted under 35 U.S.C. 154(b) by 19 days.

(21) Appl. No.: 17/233,543

(22) Filed: Apr. 19, 2021

(65) Prior Publication Data
US 2021/0330109 A1    Oct. 28, 2021

Related U.S. Application Data

(60) Provisional application No. 63/013,609, filed on Apr. 22, 2020.

(51) Int. Cl.
*A47G 25/90* (2006.01)
*A61B 42/50* (2016.01)
*A61B 42/40* (2016.01)

(52) U.S. Cl.
CPC ............ *A47G 25/904* (2013.01); *A61B 42/40* (2016.02); *A61B 42/50* (2016.02)

(58) Field of Classification Search
CPC ...... A47K 10/427; A47K 10/32; A47K 10/42; A41D 19/00; A61F 5/37; A47G 25/904; A61B 42/40; A61B 42/425; A61B 42/50
USPC ........................ 206/449; 221/303, 63, 48, 45
See application file for complete search history.

(56) References Cited

U.S. PATENT DOCUMENTS

| | | | | |
|---|---|---|---|---|
| 1,657,942 A * | 1/1928 | Spaldo | ............... | B65D 83/0847 206/746 |
| 2,020,876 A * | 11/1935 | Clark | ................... | B65D 5/5253 206/746 |
| 2,077,664 A * | 4/1937 | Beardsley | .............. | B42D 5/005 206/451 |
| 2,085,649 A * | 6/1937 | Gluck | ................ | B65D 83/0847 221/33 |
| 2,122,048 A * | 6/1938 | Shapiro | .............. | B65D 83/0805 221/45 |
| 2,604,253 A * | 7/1952 | Turner | ...................... | B65D 5/66 221/26 |
| 2,755,576 A * | 7/1956 | Golden | ...................... | G09F 3/20 40/594 |
| 3,113,673 A * | 12/1963 | Stein | .................... | B65D 5/4275 206/820 |
| 3,160,341 A * | 12/1964 | Cherney | ................ | B65D 5/067 206/815 |
| 3,209,941 A * | 10/1965 | Krake | .................. | A47K 10/421 221/302 |

(Continued)

FOREIGN PATENT DOCUMENTS

| | | | | |
|---|---|---|---|---|
| ES | 1216564 U | * | 8/2018 | ............. A47K 10/32 |
| JP | 2005515123 A | * | 5/2005 | ............. B65D 25/52 |

(Continued)

*Primary Examiner* — Rakesh Kumar
(74) *Attorney, Agent, or Firm* — White-Welker & Welker, LLC; Matthew T. Welker, Esq.

(57) ABSTRACT

The invention relates to an apparatus for dispensing of protection sheets. The protection sheets are meant for single use and are shaped to cover and protect a designated part of user's body or article, such as a palm or a finger. The apparatus is robust and easy to use. A protection sheet is dispensed as per user's requirement, which can be taken up and worn by a user to cover and prevent possible contact with a contaminated or pathogenic surface.

4 Claims, 4 Drawing Sheets

(56) References Cited

U.S. PATENT DOCUMENTS

| | | | | |
|---|---|---|---|---|
| 3,215,332 A * | 11/1965 | Bess | B65D 5/542 | 229/242 |
| 3,397,771 A * | 8/1968 | Fogle | B65D 85/187 | 229/162.6 |
| 3,482,734 A * | 12/1969 | Mierson | B65D 83/0811 | 229/242 |
| 3,554,370 A * | 1/1971 | Davis | B65D 5/725 | 229/242 |
| 3,612,264 A * | 10/1971 | Trunick | B65D 83/08 | 206/460 |
| 3,624,791 A * | 11/1971 | Taub | A47K 10/421 | 221/63 |
| 3,837,595 A * | 9/1974 | Boone | A47K 10/32 | 242/598.5 |
| 3,896,966 A * | 7/1975 | Canno | B65D 83/0852 | 221/63 |
| 4,070,489 A * | 1/1978 | Pahnke | B65D 5/545 | 426/115 |
| 4,231,491 A * | 11/1980 | Pierson | A47K 10/421 | 221/48 |
| 4,377,237 A * | 3/1983 | Pawlowski | B65D 5/5495 | 229/206 |
| 4,513,923 A * | 4/1985 | Ulics | A47K 10/38 | 242/598.5 |
| 4,537,330 A * | 8/1985 | Gelbard | B65D 33/001 | 221/302 |
| 4,793,487 A * | 12/1988 | Bentsen | B65D 75/5888 | 206/451 |
| 4,928,322 A * | 5/1990 | Bradfield | B29C 66/73921 | 2/163 |
| 5,184,728 A * | 2/1993 | Wile | A47F 13/085 | 206/493 |
| 5,269,423 A * | 12/1993 | Nguyen | B65D 33/001 | 221/45 |
| 5,297,749 A * | 3/1994 | White | A47K 10/22 | 242/597.4 |
| 5,301,832 A * | 4/1994 | Daniels | A47F 13/085 | 206/554 |
| 5,332,097 A * | 7/1994 | Wile | A47F 13/085 | 206/493 |
| 5,419,437 A * | 5/1995 | Huseman | B65B 43/26 | 383/65 |
| 5,702,081 A * | 12/1997 | Gallemore, II | G09F 7/18 | 248/219.4 |
| 5,769,213 A * | 6/1998 | Chatterton | A45C 11/34 | 206/38 |
| 5,774,889 A * | 7/1998 | Gochanour | B65H 35/002 | 2/161.7 |
| 5,975,083 A * | 11/1999 | Henderson, Jr. | A41D 13/082 | 128/878 |
| 6,202,889 B1 * | 3/2001 | Veith | B65D 83/0817 | 221/63 |
| 6,349,525 B1 * | 2/2002 | Veith | B65B 25/145 | 53/566 |
| 6,363,851 B1 * | 4/2002 | Gerhard | B41F 17/02 | 270/1.03 |
| 6,401,971 B1 * | 6/2002 | Edwards | B65D 5/5007 | 221/26 |
| 6,439,386 B1 * | 8/2002 | Sauer | B65D 5/4208 | 221/45 |
| 6,548,135 B1 * | 4/2003 | Hershey | B01J 20/28023 | 428/40.1 |
| 8,878,038 B1 * | 11/2014 | Shumaker | G10K 1/26 | 84/406 |
| D809,318 S * | 2/2018 | Hammons | | |
| 2002/0146115 A1 * | 10/2002 | Zohn | H04M 1/17 | 379/451 |
| 2004/0074941 A1 * | 4/2004 | Gochanour | A61B 42/40 | 225/54 |
| 2008/0061073 A1 * | 3/2008 | Laroche | A47K 10/421 | 221/63 |
| 2009/0057331 A1 * | 3/2009 | Fryan | B65D 83/0847 | 221/96 |
| 2011/0073612 A1 * | 3/2011 | Youssef | B42D 5/00 | 248/342 |
| 2011/0240670 A1 * | 10/2011 | Coleman | A47K 10/185 | 221/46 |
| 2011/0283439 A1 * | 11/2011 | Backhaus | A61B 42/50 | 223/111 |
| 2012/0259455 A1 * | 10/2012 | Balkin | A47K 10/32 | 221/45 |
| 2014/0284291 A1 * | 9/2014 | Sandgrund | A47F 5/0043 | 211/85.3 |
| 2015/0230672 A1 * | 8/2015 | Moskowitz | A47K 10/42 | 221/303 |
| 2020/0138130 A1 * | 5/2020 | Harrison | A61B 42/50 | |
| 2021/0330109 A1 * | 10/2021 | Safar | A61B 42/40 | |

FOREIGN PATENT DOCUMENTS

| | | | | |
|---|---|---|---|---|
| WO | WO-9815198 A1 * | 4/1998 | | A41D 13/082 |
| WO | WO-2009036499 A1 * | 3/2009 | | A41D 19/0072 |
| WO | WO-2011059941 A1 * | 5/2011 | | B65D 21/0204 |
| WO | WO-2013133964 A1 * | 9/2013 | | A47K 10/32 |
| WO | WO-2019022703 A1 * | 1/2019 | | A41D 19/0068 |

* cited by examiner

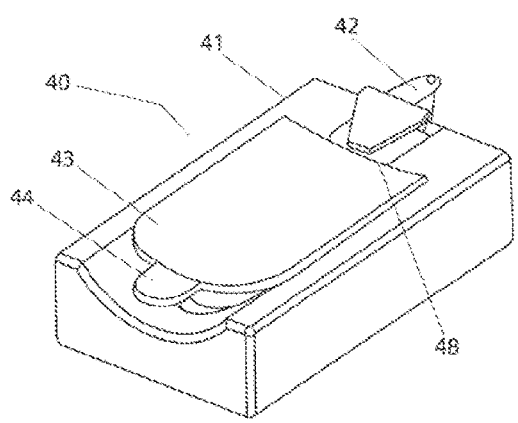
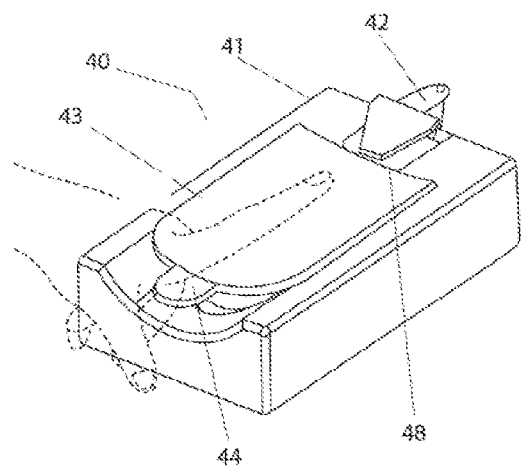
FIG. 7(a)          FIG. 7(b)
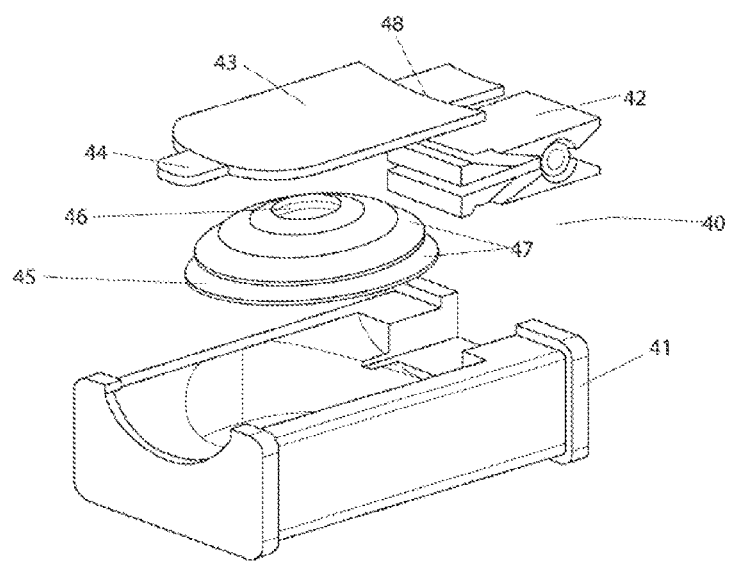
FIG. 8

PROTECTION SHEET DISPENSER

CROSS-REFERENCE TO RELATED APPLICATIONS

The present application claims priority from Provisional Application Ser. No. 63/013,609, filed Apr. 22, 2020 and entitled "Protection Sheet Dispenser". The contents of U.S. provisional patent application Ser. No. 63/013,609 are hereby incorporated by reference in entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

FIELD OF THE INVENTION

The present invention belongs to the field of apparatus for dispensing disposable protection sheets, and particularly for manual or automatic dispensing of protection sheets meant to shield or cover, a user's body parts such as a palm or a finger for protection from contamination by a pathogen.

BACKGROUND OF THE INVENTION

Several apparatus for automatic dispensing of tissues, towels and sheets have been in use. These apparatus focus on dispensing required tissues, or sheets as per a user's requirement, but do not ensure that the apparatus safely dispenses protective sheets for single-time use to a user on the go, without compromising on chances of contamination to the user by a pathogen such as a virus, bacterium, protozoan, prion, viroid, or fungus.

Below are given some of the known prior art.

U.S. Pat. No. 7,527,215 titled "Automatic tissue dispenser apparatus" describes an automatic tissue dispenser apparatus that provides for user-determined tissue length to be dispensed. The motion sensor activates and deactivates dispensing to provide user control. A cutting edge is provided for tearing tissue as chosen. A hand crank is optionally provided to negate dysfunction in the event of power or component failure. A stanchion with base is optionally provided for a free-standing dispenser.

U.S. Pat. No. 3,009,604 titled "Flexible sheet dispenser" utilizes a utilizing pulley drive means for dispensing of paper towels, napkins, wrapping material and other flexible sheet members. The apparatus is capable of dispensing individual flat sheets from a stack.

U.S. Pat. No. 6,375,034 titled "Glove dispenser" discloses an improved glove dispenser that permits a user to don gloves without first touching their exterior. The disclosed device includes a plurality of gloves attached by their cuffs to a filament, with the filament and cuffs being dispensed from an exchangeable glove cartridge. The invention provides a new method for donning gloves that can prevent user contamination of the gloves by touching the exterior of the gloves during the donning process.

Despite various improvements and progress in the field, some of the major obstacles that still exist are presented herein below. The existing devices are unable to overcome the limitations of providing a safe, contact free, simple to use apparatus for dispensing single time use protection sheets such as wearable covers for protecting palm or fingers of a user while working in a public place such as for example, a fuel refilling pump station, handles of doors, key pads of machines and payment terminals such as bank ATM, credit card machines, in order to restrict the transmission of virus, microbes and other such pathogens.

When people try to wear protective clothing such as disposable sterilized gloves in order to prevent the transmission of bacteria or other contaminants to themselves and to others, they generally access these gloves to be dispensed from a common box similar to those used to dispense disposable facial tissues. Normally, the individual typically grabs a glove and pulls it from the box using an uncovered hand. Using one ungloved hand, the user slips the glove on to the other hand, after which the gloved hand is used to grab the second glove from the box and then to don it upon the ungloved hand. This method requires that the first glove and the glove dispenser have to be touched by ungloved hands. Thus neither the first glove can be expected to be clean, nor the second one. Such a chain of actions leads to unknowing spreading of infectious diseases and pandemics.

Accordingly, improvements are needed in the existing devices that negate the above shortcomings. It is observed that the purpose and methodology of all the above inventions that are part of prior art do not envisage the unique embodiment of a easy to use, convenient and safe apparatus for dispensing protective, wearable, disposable protection sheets or covers for palm, fingers, footwear and the like, as described in the present application. The scope of the invention is to be determined by the terminology of the following description, drawings and the legal equivalents thereof.

SUMMARY OF THE INVENTION

The present invention may be summarized, at least in part, with reference to its objects.

It is therefore a primary objective of the present invention to provide an apparatus for dispensing of protection sheets that can be easily and safely taken and worn by a user on the go while coming in contact with surfaces with potential pathogenic contamination, and thereby reduce transmission of pathogens.

Another objective of the present invention is to provide an apparatus for dispensing of protection sheets that are disposable and single-in-use in nature.

Another objective of the present invention is to provide a rugged and robust apparatus for dispensing of protection sheets without minimal human contact.

Yet another objective of the present invention is to provide an apparatus for dispensing of protection sheets that can be taken and worn by a user to cover and protect specific body parts or wearable articles, such as palms, fingers, thumbs, footwear, and thus act as palm protectors, finger protectors, thumb protectors, or footwear protectors.

The invention described herein is an apparatus for dispensing of protection sheets, and is explained through four main embodiments, namely: Roller mounted palm sheet dispenser, Releasably retained tear-and-pull away palm sheet dispenser, Roller mounted finger sheet dispenser, Releasably retained tear-and-pull away finger sheet dispenser.

The above summary is intended to illustrate exemplary embodiments of the invention, which will be best understood in conjunction with the detailed description to follow, and are not intended to limit the scope of the invention. Additional objects and embodiments of the invention will be set forth in part in the description which follows, and in part will become apparent to those skilled in the art upon examination of the following, or may be learned by practice of the invention. Thus these and other objects of the present invention will be more readily apparent when considered in reference to the following description and when taken in conjunction with the accompanying drawings.

DESCRIPTION OF THE DRAWINGS

FIGS. 7(a) and 7(b) are illustrative views of the present invention in a fourth embodiment of the present invention, referred to as "Releasably retained tear-and-pull away finger sheet dispenser".

FIG. 8 is an illustrative exploded view of the present invention in a fourth embodiment of the present invention, referred to as "Releasably retained tear-and-pull away finger sheet dispenser".

DETAILED DESCRIPTION OF THE INVENTION

As required, detailed embodiments of the present invention are disclosed herein. However, it is to be understood that the disclosed embodiments are merely exemplary of an invention that may be embodied in various and alternative forms. Therefore, specific functional details disclosed herein are not to be interpreted as limiting, but merely as a representative basis for the claims and/or as a representative basis for teaching one skilled in the art to variously employ the present invention.

The following description is presented to enable any person skilled in the art to make and use the invention, and is provided in the context of particular applications of the invention and their requirements.

For purpose of clarity, the following definitions of terms are used in this specification.

The term "finger" refers to any digit on a hand including, but not limited to, a thumb, an index finger, middle finger, ring finger, or a pinky finger, of a user.

The invention is presently described in terms of four main embodiments. A first embodiment of the invention is referred to as "Roller mounted palm sheet dispenser" for clarity. A second embodiment of the invention is referred to as "Releasably retained tear-and-pull away palm sheet dispenser" for clarity. A third embodiment of the invention is referred to as "Roller mounted finger sheet dispenser" for clarity. A fourth embodiment of the invention is referred to as "Releasably retained tear-and-pull away finger sheet dispenser" for clarity.

It will be well understood to a person skilled in the art that other embodiments using the same inventive concept can be applied for dispensing protection sheets for items such as shoe covers, footwear and the like.

Accordingly, the first embodiment of the present invention, designated as "Roller mounted palm sheet dispenser" is an apparatus for dispensing of protection sheets mainly designated for the protection of a palm of a user, when the apparatus is generally placed on a horizontal surface, such as, by way of example, a table top. The first embodiment is presently described with reference to FIGS. 1(a), 1(b) and 2.

Figures 1A, 1B:
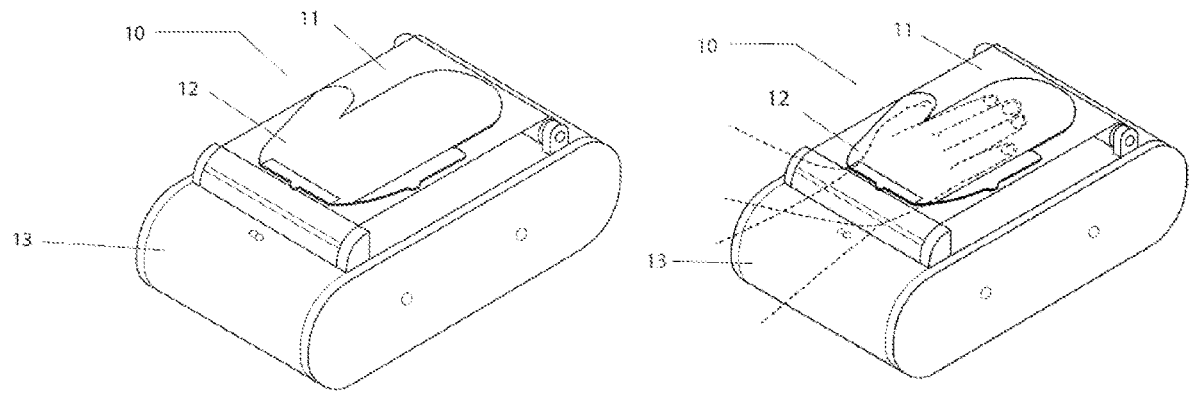
FIGS. 1(a) and 1(b) are illustrative views of the present invention in a first embodiment of the present invention, referred to as "Roller mounted palm sheet dispenser".

FIGS. 1(a) and 1(b) depict the first embodiment, wherein the apparatus 10 includes a base enclosure 13. 11 denotes a roll mounted on the base enclosure 13. The roll 11 includes a detachable palm shaped protection sheet denoted by 12.

FIG. 1(b) depicts the first embodiment with the dotted lines showing a user's palm placed on the apparatus 10.

Figure 2:
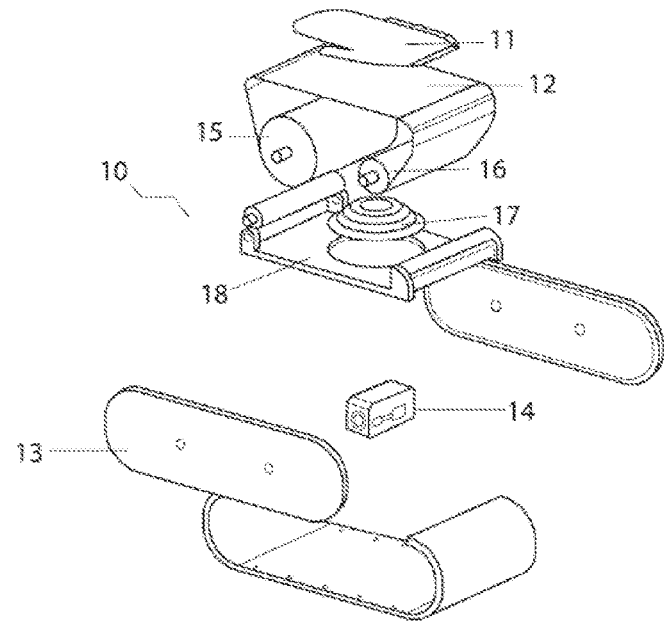
FIG. 2 is an illustrative exploded view of the present invention in a first embodiment of the present invention, referred to as "Roller mounted palm sheet dispenser".

FIG. 2 depicts an exploded view of the first embodiment. The apparatus 10 includes a base enclosure 13, a roll 11, a plurality of detachable palm shaped protection sheets 12, a power source 14, a plurality of rollers 15 and 16, a suction dome unit 17 of resilient material, and a support member 18.

The suction dome unit 17 comprises of a plurality of elliptically shaped, concentric folds, having interspacing gaps, and arranged in a convex curvature (generally shaped like an egg), having a slight depression on top, and configured to fit with a user's palm concavity and enable the user to easily grip the uppermost single protection sheet. When contact pressure is applied by the user's palm, on the top depression of the suction dome unit, the internal volume of the suction dome unit is compressed such that air is uniformly released along all the interspacing gaps of the plurality of elliptically shaped concentric folds, thereby causing uniform suction on the plurality of detachable palm shaped protection sheets 12, positioned above the top depression of the suction dome unit 17. After the uppermost single protection sheet adheres to the user's palm and contact pressure is released, air again enters the suction dome unit via the interspacing gaps of the plurality of elliptically shaped concentric folds and the resilient material of the suction dome unit causes it to return to its relaxed condition, and the plurality of protection palm shaped protection sheets return to the original position.

Accordingly, the first embodiment of the present invention, referred to as a roller mounted palm sheet dispenser, provides an apparatus for dispensing of pathogen protection sheets, the apparatus comprising:

a base enclosure configured for being placed on a generally horizontal surface, the base enclosure further comprising:
  a roll of sheet, a power source, a plurality of rollers, a support member, and a suction dome unit;

wherein
the roll of sheet is rotatably mounted on the plurality of rollers and configured to be powered by the power source;
the roll of sheet further comprising of a plurality of detachable palm shaped protection sheets;
wherein each protection sheet comprises: a front adhesive surface, a back non-adhesive waxed surface, and is capable of removable detachment, after application of contact pressure by a user's palm;
the suction dome unit being non-removably affixed to the support member;
the suction dome unit further comprising of a plurality of elliptically shaped, concentric folds with interspacing gaps, arranged in a convex curvature, characterized by a top, central depression, and configured to fit with a user's palm concavity,
and the suction dome unit facilitates adhering and removal of the detachable palm shaped protection sheet from the roll of sheet to the user's palm, on application of pressure by the user and subsequent release of pressure by the user.

The second embodiment of the present invention, designated as "Releasably retained tear-and-pull away palm sheet dispenser" is an apparatus for dispensing of protection sheets mainly designated for the protection of a palm of a user. This embodiment may be placed in the vertical direction, such as being mounted on a wall surface, as well as in the horizontal direction such as, by way of example, a table top. The second embodiment is presently described with reference to FIGS. 3(a), 3(b), 3(c) and 4.

Figure 3A:
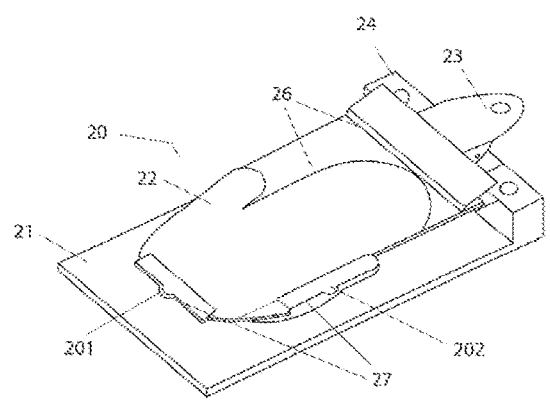
FIGS. 3(a) and 3(b) are illustrative views of the present invention in a second embodiment of the present invention, referred to as "Releasably retained tear-and-pull away palm sheet dispenser".
Figure 3B:
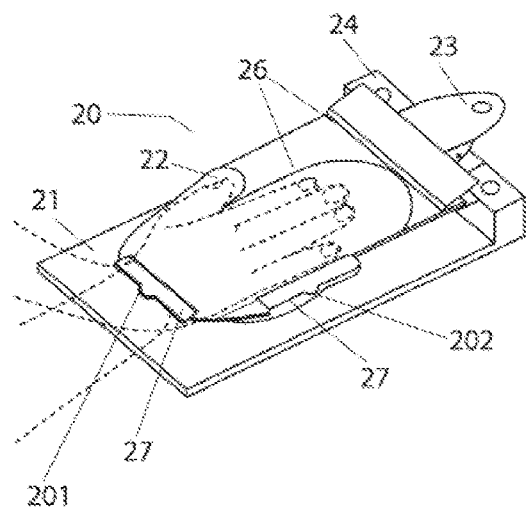

FIGS. 3(a) and 3(b) depict the second embodiment, wherein the apparatus 20 includes a plurality of sheets 21, each sheet having a detachable palm shaped protection area 22, a supporting base structure 24, a hanger unit 23. Each detachable protection area 22 has a perforated edge 26, at least one foldable area 27, pull away tab areas 201 and 202.

FIG. 3(b) depicts the second embodiment with the dotted lines showing a user's palm placed on the apparatus 20.

Figure 3C:
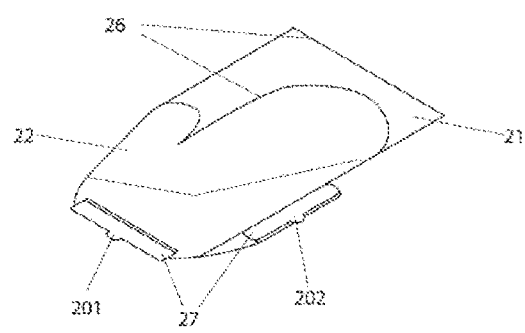
FIG. 3(c) is an illustrative view of a protective palm sheet in accordance with the second embodiment of the present invention.
Figure 4:
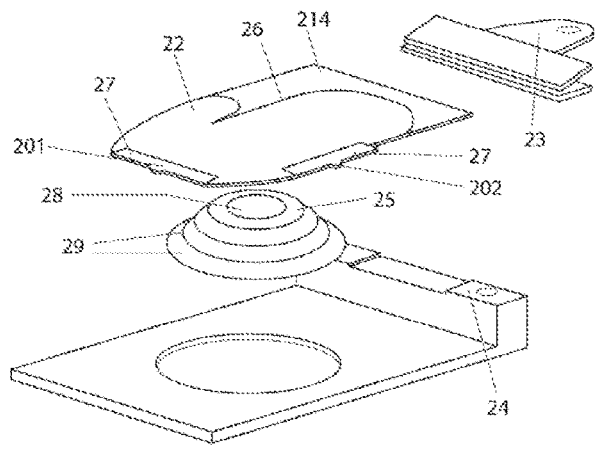
FIG. 4 is an illustrative exploded view of the present invention in a second embodiment of the present invention, referred to as "Releasably retained tear-and-pull away palm sheet dispenser".

FIG. 3(c) depicts the protection sheet 21 in accordance with the second embodiment of the present invention. The protection sheet 21 includes at least one foldable area 27 (by way of example, two foldable areas are shown in the drawing), at least one perforated edge 26, pull away tab areas 201 and 202, FIG. 4 depicts the second embodiment, in an exploded view, wherein the apparatus 20 includes a plurality of sheets 21, each sheet having a detachable palm shaped protection area 22, a supporting base structure 24, a hanger unit 23, a suction dome unit 25. Each detachable protection area 22 has at least one perforated edge 26, at least one foldable area 27, and at least one pull away tab area. By way of example, two tab areas are depicted in the second embodiment shown in the drawing.

The hanger unit 23 provides a means of suspending the apparatus 20 from a vertical surface, such as a wall.

In alternate embodiments, the apparatus 20 may be placed on a horizontal surface such as a table top, or counter top.

The suction dome unit 25 comprises of a plurality of elliptically shaped, concentric folds 29, having interspacing gaps, and arranged in a convex curvature (generally shaped like an egg), having a slight central depression on top 28, and configured to fit with a user's palm concavity and enable the user to easily grip the uppermost single protection sheet. When contact pressure is applied by the user's palm, on the top depression of the suction dome unit, the internal volume of the suction dome unit is compressed such that air is uniformly released along all the interspacing gaps of the plurality of elliptically shaped concentric folds, thereby causing uniform suction on the plurality of detachable palm shaped protection sheets 21, positioned above the top depression of the suction dome unit 25. After the uppermost single protection sheet adheres to the user's palm and contact pressure is released, air again enters the suction dome unit via the interspacing gaps of the plurality of elliptically shaped concentric folds and the resilient material of the suction dome unit causes it to return to its relaxed condition, and the plurality of palm shaped protection sheets return to the original position.

The protection area 22 is preferably shaped like a mitten, a glove, or like a palm. One or more foldable area 27 is also provided to suit users with larger sized palms, or left handed users. Pull away tab area 201 and 202 are also provided.

The plurality of sheets 21 is removably bunched together along an edge, preferably by adhesive means. The means of removal is facilitated by a perforated edge. Each sheet has a front surface and a back surface. The front surface of the palm shaped protection area 22, is coated by a mild, safe, non-allergic adhesive material. The back surface is coated by a waxy non-adhesive material. This ensures that the protection sheets do not stick to each other and a single sheet can be easily peeled off, and detached along the perforated edge and thereby separated from the remaining bunch by a user.

In alternate embodiments, each protection area also has a pull-away tab area, which is a small area having no adhesive material on the front surface, and no material coated on the back surface as well. The pull-away tab area is meant for removal or peeling away the protection sheet for disposal after use to avoid any contact with contaminated surface of the soiled protection sheet. Two pull-away tab areas are shown in the drawings, by way of example.

Each sheet with palm shaped protection area also has a marked perforated edge, which helps a user to easily tear off the sheet and separate it from the rest of the bunch. The user can use the pull-away tab area or the perforated edge for detaching the sheet from the bunch.

The suction dome unit is made of resilient elastic material. It is curved in shape and has a slight depression in the centre. The suction dome unit is non-removably affixed to the supporting dispensing member of the hanger unit. The function of the suction dome unit is to hold the plurality of protection sheets in place after the top most sheet has been dispensed.

When a user requires a protection sheet, he or she places the palm over the top most protection sheet and presses the plurality of protection sheets. The suction dome unit gets pressed and acts like a suction cup with air being released from the interspacing gaps in a uniform manner, and pulls back the stack i.e. the plurality of protection sheets, inside, while the top most protection sheet adheres to the palm of the user. The user then pulls away the top most protection sheet along the perforated edge (or the pull-away tab optionally) and releases pressure on the rest of the plurality of protection sheets. The suction dome unit then returns it its original shape and the plurality of protection sheets is restored to the earlier position wherein the sheets are held together in a bunch yet optimally separated for easy removal by the user.

The hanger unit can be affixed or mounted on a surface such as a wall or a door, or it can be hung or suspended by means such as a hook in locations where there is possibility of contact and contamination by many people, such as fuel refilling station, doors handles etc.

Accordingly, the second embodiment of the present invention, referred to as the wall mounted pull away palm sheet dispenser provides an apparatus for dispensing of protection sheets, the apparatus comprising:

(a) a hanger unit, capable of being mounted on a vertical surface,
(b) a supporting base structure,
(c) a plurality of sheets being coupled to the hanger unit, each sheet having a detachable palm shaped protection area, at least one perforated edge, wherein each protection area is characterized by a front adhesive surface, a back non-adhesive waxed surface, at least one foldable area, and at least one pull-away tab area,
(d) a suction dome unit, said suction dome unit non-removably affixed to the supporting base structure, wherein the suction dome unit comprises of a plurality of elliptically shaped, concentric folds with interspacing gaps, arranged in a convex curvature, characterized by a top, central depression, and configured to fit with a user's palm concavity, wherein each palm shaped protection area is being capable of removable detachment along the perforated edge, after application of contact pressure by a user, and the suction dome unit holds the plurality of protection sheets closely in place on application of pressure by the user and loosens the plurality of protection sheets on release of pressure by the user.

In a third embodiment of the present invention referred to as "Roller mounted finger sheet dispenser", is an apparatus for dispensing of protection sheets mainly designated for the protection of a finger or a thumb of a user, when the apparatus is generally placed in the horizontal direction, such as by way of example, a table top. The third embodiment is presently described with reference to FIGS. 5(a), 5(b) and 6.

Figure 5A:
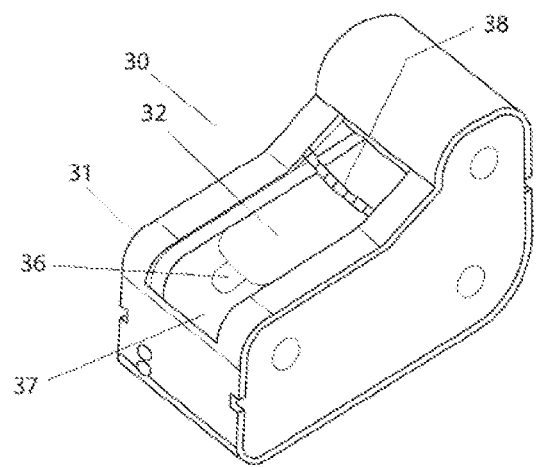
FIGS. 5(a) and 5(b) are illustrative views of the present invention in a third embodiment of the present invention, referred to as "Roller mounted finger sheet dispenser".
Figure 5B:
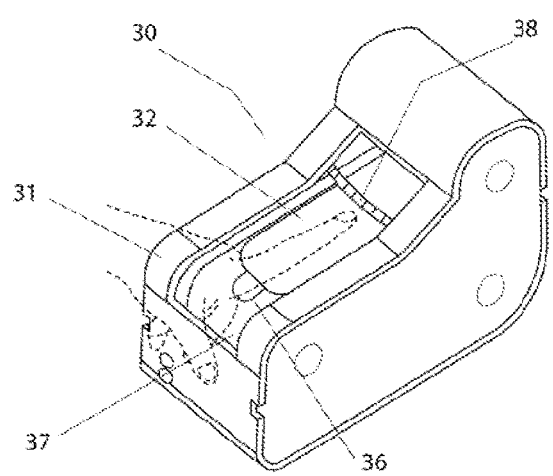

FIGS. 5(a) and 5(b) depict the third embodiment, wherein the apparatus 30 includes a base enclosure 31. 37 denotes a roll mounted on the base enclosure 31. The roll 37 includes a detachable finger shaped protection sheet denoted by 32, and a pull away tab area 37. 38 depicts an alignment member positioned on the roll 37. Alignment member 38 is a curved wire passing through a plurality of tiny rollers for easy movement of the roll 37.

FIG. 5(b) depicts the third embodiment with the dotted lines showing a user's finger placed on the apparatus 30.

Figure 6:
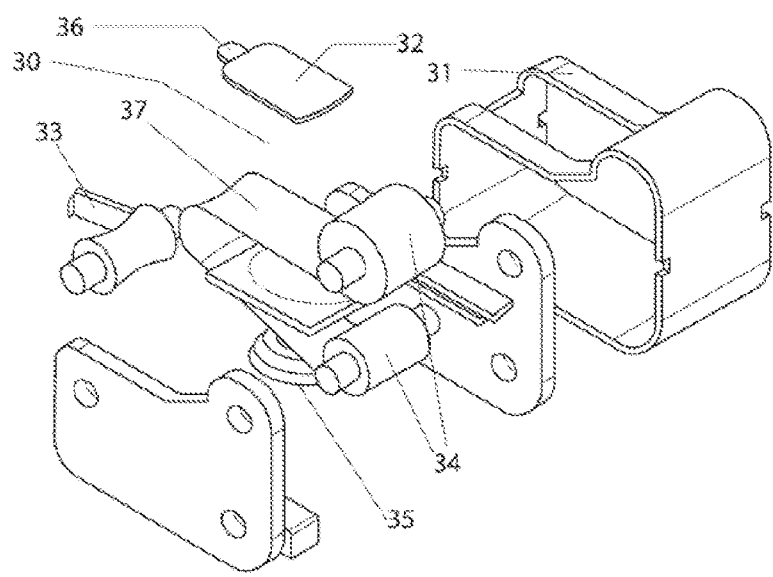
FIG. 6 is an illustrative exploded view of the present invention in a third embodiment of the present invention, referred to as "Roller mounted finger sheet dispenser".

FIG. 6 depicts an exploded view of the third embodiment. The apparatus 30 includes a base enclosure 31, a roll 37, a plurality of detachable finger shaped protection sheets 32 having a pull away area 36, a power source 33, a plurality of rollers 34, a suction dome unit 35.

In the third embodiment, the protection sheets are shaped as a finger or a thumb. Preferably, they are shaped as the index finger. The plurality of protection sheets is stacked on a concave shaped back apparatus instead of the hanger unit of the first embodiment. The concave shaped back apparatus is made of a resilient material and is provided with a miniature domed-shape suction member in the middle. Protection sheets are coated with non-allergenic adhesive on the front surface and the back surface is coated with a non-stick waxy material.

The suction dome unit 35 comprises of a plurality of elliptically shaped, concentric folds, having interspacing gaps, and arranged in a convex curvature (generally shaped like an egg), having a slight central depression on top, and configured to fit with a user's finger and enable the user to easily grip the uppermost single protection sheet. When contact pressure is applied by the user's finger, on the top depression of the suction dome unit, the internal volume of the suction dome unit is compressed such that air is uniformly released along all the interspacing gaps of the plurality of elliptically shaped concentric folds, thereby causing uniform suction on the plurality of detachable finger shaped protection sheets 32, positioned above the top depression of the suction dome unit. After the uppermost single protection sheet adheres to the user's finger and contact pressure is released, air again enters the suction dome unit via the interspacing gaps of the plurality of elliptically shaped concentric folds and the resilient material of the suction dome unit causes it to return to its relaxed condition, and the plurality of finger shaped protection sheets return to the original position.

Accordingly, the third embodiment of the present invention, referred to as the roller mounted finger sheet dispenser provides an apparatus for dispensing of protection sheets, the apparatus comprising:

a base enclosure configured for being placed on a generally horizontal surface, the base enclosure further comprising:
a roll of sheet, an alignment member positioned on the roll, a power source, a plurality of rollers, a support member, and a suction dome unit;
wherein the roll of sheet includes a plurality of detachable finger shaped protection sheets, the roll of sheet being rotatably mounted on the plurality of rollers and configured to be powered by the power source;
wherein each protection sheet is characterized by, a front adhesive surface, a back non-adhesive waxed surface, and being capable of removable detachment after application of contact pressure by a user's finger;
wherein the suction dome unit is non-removably affixed to the support member, the suction dome unit further comprising of a plurality of elliptically shaped, concentric folds with interspacing gaps, arranged in a convex curvature, characterized by a resilient material and having a top, central depression, and configured to fit with a user's finger.

Each finger protection sheet is provided with at least one pull-away tab area. Further each sheet has a front adhesive surface and a back non-adhesive waxy surface. The pull-away tab area is not coated with any material on the front or the back surfaces and is intended to help the user peel away the soiled sheet after use, or optionally even while detaching the top most protection sheet from the rest of the plurality of protection sheets.

In a fourth embodiment of the present invention referred to as "Releasably retained tear-and-pull away finger sheet dispenser", an apparatus for dispensing of protection sheets mainly designated for the protection of a finger or a thumb of a user, is provided. The apparatus may be placed in the vertical direction, such as by way of example, by being suspended against a wall, or in a horizontal direction such as a table top. The fourth embodiment is presently described with reference to FIGS. 7(a), 7(b) and 8.

FIGS. 7(a) and 7(b) depicts the fourth embodiment, wherein the apparatus 40 includes a plurality of sheets 43, each sheet having a detachable finger shaped protection area, a pull away tab area 44, a detachable perforated edge 48, a supporting base structure 41, a hanger unit 42.

FIG. 7(b) depicts the fourth embodiment with a user's fingers in dotted lines, and being placed on apparatus 40.

FIG. 8 depicts the fourth embodiment, in an exploded view, wherein the apparatus 40 includes a plurality of sheets 43, each sheet having a detachable finger shaped protection area, a pull away tab area 44, a detachable perforated edge 48, a supporting base structure 41, a hanger unit 42, a suction dome unit 45.

Accordingly, the fourth embodiment of the present invention, referred to as the releasably retained tear-and-pull away finger sheet dispenser provides an apparatus for dispensing of protection sheets, the apparatus comprising:
- (a) a hanger unit, capable of being mounted on a vertical surface,
- (b) a supporting base structure,
- (c) a plurality of sheets being coupled to the hanger unit, each sheet having a detachable finger shaped protection area, at least one perforated edge, a pull away tab area, wherein each protection area is characterized by a front adhesive surface, and a back non-adhesive waxed surface,
- (d) a suction dome unit, said suction dome unit non-removably affixed to the supporting base structure, the suction dome unit further comprising of a plurality of elliptically shaped, concentric folds with interspacing gaps, arranged in a convex curvature, characterized by a resilient material and having a top, central depression, and configured to fit with a user's finger,
  wherein each finger shaped protection area is being capable of removable detachment along the perforated edge, after application of contact pressure by a user,
  and the suction dome unit holds the plurality of protection sheets closely in place on application of pressure by the user and loosens the plurality of protection sheets on release of pressure by the user.

In all the embodiments, the adhesive material coated on the front surface of the protection sheet has specific material properties to indicate if it has been previously used and has been soiled or contaminated.

All references to the protection sheets in this application are exemplary in nature and the same principles as that of the present invention are not limited to protection of palms, or fingers but can be applied to other articles or body parts as well such as, protection sheets meant to cover feet, footwear etc.

The invention is robust and rugged. It can be installed on various locations for people to pick up a wearable, disposable protection sheet on the go.

In alternate embodiments, the protection sheets may be coated with a disinfectant material on the back surface.

In alternate embodiments, the protection sheets may be provided with multiple foldable areas to accommodate the protection sheets in limited space.

In alternate embodiments, the protection sheets may be provided with different configurations of perforated edges to accommodate easy removal of the protection sheets by a user.

In alternate embodiments, the protection sheets may be provided with specific features on the back surface such as bristles or fibres.

In alternate embodiments, the protection sheets may be provided with specific visual features on the front back surface, such as a different colour, text, design or other graphic features.

In alternate embodiments, the protection sheets may be coated with material having specific functional properties, on the back surface, such as soap, detergent, disinfectant or surfactant agents.

In alternate embodiments, the protection sheets may be coated with functional materials which show a visual change, such as change in colour, post single use.

In alternate embodiments, the apparatus may be used for dispensing wearable articles such as gloves, and need not be limited to protection sheets.

In alternate embodiments, the apparatus may be used for dispensing protection sheets, which may be used for cleaning or wiping surfaces.

In alternate embodiments, the apparatus may be provided with features for dispensing wearable articles such as safety goggles, face masks, head gear.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

What is claimed is:

1. A roller mounted palm sheet dispensing apparatus for dispensing of pathogen protection sheets, the apparatus comprising:
   a base enclosure configured for being placed on a generally horizontal surface, the base enclosure further comprising:
      a roll of sheet, a power source, a plurality of rollers, a support member, and a suction dome unit;
      wherein
         the roll of sheet is rotatably mounted on the plurality of rollers and configured to be powered by the power source;
         the roll of sheet further comprising of a plurality of detachable palm shaped protection sheets;
            wherein each protection sheet comprises: a front adhesive surface, a back non-adhesive waxed surface, and is capable of removable detachment, after application of contact pressure by a user's palm;
         the suction dome unit being non-removably affixed to the support member;
         the suction dome unit further comprising of a plurality of elliptically shaped, concentric folds with interspacing gaps, arranged in a convex curvature, comprising a top, central depression, and configured to fit with a user's palm concavity, and
      the suction dome unit facilitates adhering and removal of the detachable palm shaped protection sheet from the roll of sheet to the user's palm, on application of pressure by the user and subsequent release of pressure by the user.

2. An apparatus as claimed in claim 1, wherein the protection sheet is provided with at least one foldable area.

3. An apparatus as claimed in any of the claim 1 or 2, wherein the protection sheet is coated with a material selected from a group comprising of detergent, disinfectant or surfactant agents, and color changing materials.

4. An apparatus as claimed in any of the claim 1 or 2, wherein the apparatus dispenses sheets for wiping and cleaning of contaminated surfaces.

* * * * *